United States Patent [19]
Haines et al.

[11] Patent Number: 5,551,355
[45] Date of Patent: Sep. 3, 1996

[54] NEEDLE INCINERATOR

[76] Inventors: Ralph Haines, 61 Morrell Street, Brantford, Ontario, Canada, N3T 4J3; Klaus Heidelberger, 82 Glenburn Drive, Waterloo, Ontario, Canada; Brian Lang, 39 Greenwood Trail, Brantford, Ontario, Canada; William D. Mitchell, C/O 85 Inglis Street, Ayr, Ontario, Canada, N0B 1E0; Petar Stancu, Unit 3, 81 Eagan Drive, Kitchener, Ontario, Canada, N2M 5C7

[21] Appl. No.: 431,836

[22] Filed: May 1, 1995

[51] Int. Cl.⁶ ................................................. F23G 5/00
[52] U.S. Cl. .................... 110/242; 110/346; 219/68
[58] Field of Search ............................ 110/242, 236, 110/345, 346, 250; 219/68

[56] References Cited

U.S. PATENT DOCUMENTS

| | | | |
|---|---|---|---|
| 4,495,873 | 1/1985 | Blankenship | 110/242 |
| 4,628,169 | 12/1986 | Ching-Lung . | |
| 4,877,934 | 10/1989 | Spinello | 219/68 |
| 4,961,541 | 10/1990 | Hashimoto . | |
| 4,965,426 | 10/1990 | Colombo | 219/68 |
| 5,075,529 | 12/1991 | Kudo | 219/10.77 |
| 5,076,178 | 12/1991 | Kohl et al. | 110/346 |
| 5,091,621 | 2/1992 | Butler | 219/68 |
| 5,138,125 | 8/1992 | Salesses | 219/68 |
| 5,282,428 | 2/1994 | Greville et al. | 110/250 |
| 5,288,964 | 2/1994 | Walker et al. | 219/68 |
| 5,300,752 | 4/1994 | Elmerick et al. | 219/68 |
| 5,336,862 | 8/1994 | Yelvington . | |
| 5,385,105 | 1/1995 | Withers, Jr. et al. | 110/242 |

*Primary Examiner*—Thomas N. Moulis
*Attorney, Agent, or Firm*—Dowell & Dowell

[57] ABSTRACT

An apparatus for incinerating the metal shaft of hypodermic needles which includes a housing having adjustable electrodes mounted therein which when supplied with electric current and contacted with a metal shaft of a needle will instantly disintegrate the needle to a safe residue which is collected in a tray within the housing. Gases generated within the housing from the incineration process are purified by passing through filters and ionizers before being vented to atmosphere.

20 Claims, 7 Drawing Sheets

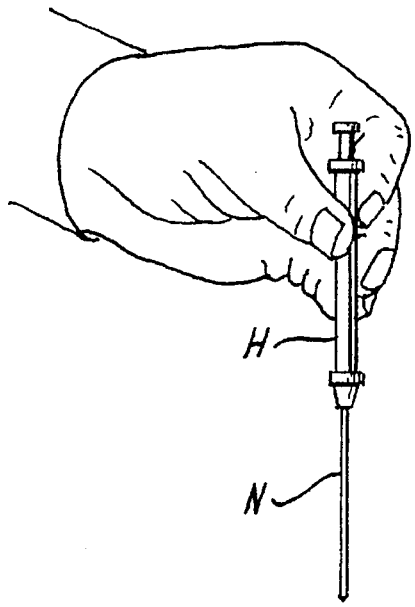
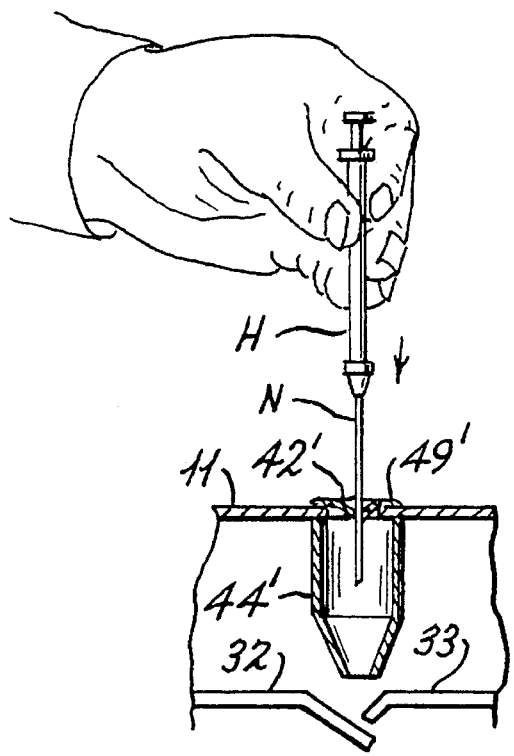
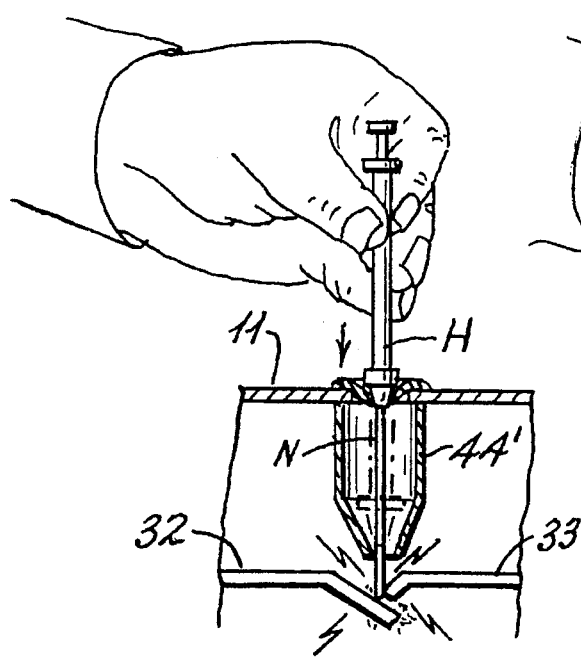
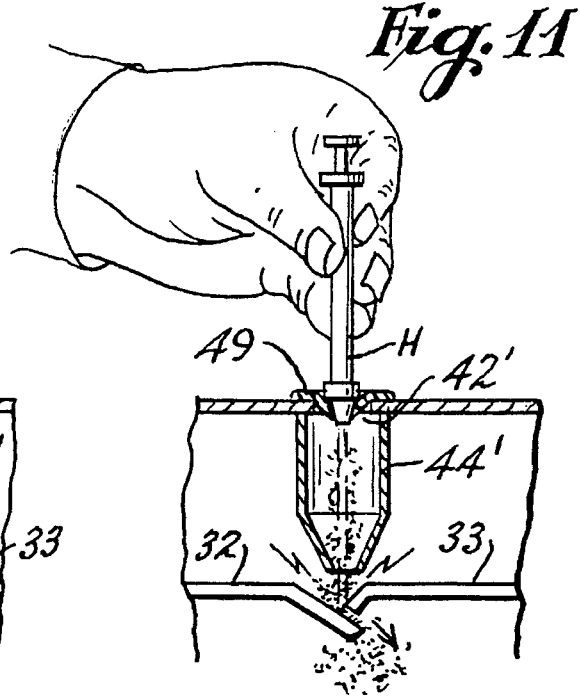

NEEDLE INCINERATOR

BACKGROUND OF THE INVENTION

1. Field of the Invention

This invention is generally directed to incinerating devices and more specifically to devices for disintegrating metal needles associated with hypodermic syringes of a type which include a pair of electrodes which are connected to a suitable source of electrical power, such as a conventional 110 volt AC outlet.

2. History of the Related Art

With the ever increasing need to prevent the spread of infectious diseases, there has been a growing emphasis on the safe handling and disposal of medical waste and particularly the needles utilized with hypodermic syringes. It is extremely important to protect medical personnel and others who are required to administer hypodermic injections as well as those who must dispose of the waste by products including the hypodermic syringes and needles, from accidental "stick" injuries which can occur by the improper or accidental handling of such waste products after they have been used.

In this respect, some hypodermic manufacturers began experimenting with syringes having retractable needles which, after a syringe had been used, automatically withdraw the needle into the barrel of the syringe to prevent accidental contact with the tip of the needle. Unfortunately, although retracting syringes offer a degree of safety not available with conventional syringes, the added costs of such syringes are prohibitive. In addition, in disposing of a syringe having a needle stored therein, if the body of the syringe becomes fractured, it is still possible that an accidental injury may be caused by the metallic needle.

In an effort to provide increased safety and prevent the infectious spread of disease, in recent years small incinerating devices have been developed which are specifically designed for destroying hypodermic syringe needles. Most of these incinerating devices have been designed to be portable and most operate on conventional 110 volt AC outlet current so that the units may be plugged into an outlet in an examination room or other room where injections are given. In this manner, a needle may be destroyed immediately after its use by inserting the metal needle, attached to the hypodermic syringe, into the incinerating apparatus where heat or electricity is utilized to thermally neutralize, melt, or disintegrate the needle. Some examples of such incinerators are found in U.S. Pat. Nos. 5,075,529 to Kudo, 4,628,169 to Ching-Lung, 4,877,934 to Spinello, 4,965,426 to Colombo, 5,282,428 to Grevill et al., 5,288,964 to Walker et al., 5,091,621 to Butler, 5,138,125 to Salesses, 5,300,752 to Elmerick et al. and 5,336,862 to Yelvington.

In many of the prior art incinerators, a pair of electrodes are engageable by a needle inserted into the incinerator housing. An electric arc is established through the needle destroying the needle at temperatures of 1,000° C. or higher with the disintegration occurring substantially instantaneously. In some of the prior art incinerators small fans are utilized to exhaust the products of combustion to atmosphere. To prevent the release of airborne contaminants or pathogens which may remain in the gaseous material, some prior art devices utilize a filter element to filter the air before it is exhausted from the incinerator apparatus. To further aid in the processing of the gaseous by-products of an incineration process, U.S. Pat. No. 5,288,964 also discloses the use of an electronic precipitator for treating the exhaust gas before it is exhausted through a gas filter system.

Unfortunately, prior art needle incinerating units have not met with acceptance of practitioners in the health care industry. Incinerating devices have not proven to be sufficiently capable of ensuring that all exhaust from the incinerating devices is purified to prevent smoke, toxins, trace metal contaminates, and airborne pathogens from being discharged to atmosphere. Practitioners are weary of placing any type of incinerating apparatus within an enclosed area in which people are exposed to the exhaust. In addition, as the incinerators are easily accessible to patients when left unattended in a room, there is a possibility of unauthorized use or tampering of the units. Accidental contact with the electrodes of the incinerators with any metal object held by a patient or other person could result in serious injury. The possible product and civil liabilities which could result detract from the acceptance of incinerators in a working environment.

Another feature which the prior art has not fully appreciated is the need to provide for adjustment of the incinerator electrodes or contacts depending upon the type of needle which is to be destroyed. In many prior art incinerators, the electrodes for contacting the needle are fixed relative to one another or flexible relative to one another, so as to ensure contact with varying lengths of needles.

Also, prior art needle incinerators have not been adequately designed to cooperatively destroy needles associated with differing sizes of hypodermic syringes.

In view of the foregoing, there is a need to increase the operating performance, safety characteristics, exhaust treatment characteristics, and adaptability of needle incinerators.

SUMMARY OF THE INVENTION

This invention is directed to an electrical incinerator for destroying metal needles associated with hypodermic syringes wherein the incinerator includes a housing including a cover which is pivotably mounted and selectively locked to a base. Mounted interiorly of the housing are a pair of spaced but adjustable electrodes or electrical contacts which are connected through a transformer to a source of AC power supply. The contacts are spaced in alignment beneath a syringe tube opening in the cover of the housing which, in the preferred embodiment, includes a tapered guide sleeve which is designed to engage the periphery of the end of the syringe when a needle extending from the syringe is inserted within the opening so as to limit the degree to which the syringe may be inserted and to also limit or prevent the escape of gases from within the housing when a needle is incinerated and to prevent any arc or spark from reaching the opening. In the preferred embodiment, an indexing device is placed on the top of the housing in line with the syringe opening thereby creating channels into the housing for syringes of varying sizes.

In order to filter and purify all the combustion gases generated during the incineration process, the present invention includes a plurality of spaced filter elements capable of removing a majority of particles in the air. In one embodiment, the filter elements are placed both upstream and downstream of the combustion chamber in which the adjustable electrodes or contacts are mounted so as to initially pre-filter air entering the chamber and thereafter filter the combustion gases being conveyed to exhaust. The present invention also incorporates a pair of high voltage ionizers which function to remove any trace elements and particles in the exhaust gas before the air is exhausted to atmosphere by a pair of fans which draw the air through the unit thereby creating a positive air flow out of the combustion chamber during the incineration process.

The incinerator utilizes a first safety switch which automatically terminates power to the unit in the event the cover of the housing is opened. Also, to activate the unit, the operator, in the preferred embodiment, must have an access key or other device so that it is not possible to accidentally turn the unit ON.

The unit further incorporates a main transformer for powering the electrical contacts and a secondary transformer for providing high voltage to the ionizers and a step down voltage to the fans.

It is the primary object of the present invention to provide a small and portable electrically operated needle incinerator device which may be utilized in substantially any environment, including clean air environments, wherein the exhaust gases from the incinerator are both filtered and ionized prior to being exhausted to atmosphere so that the exhausted air meets health and clean room standards.

It is also an object of the present invention to provide a small electrically operated incinerator device which incorporates adjustable electrical contacts for engaging a needle attached to a hypodermic syringe so that when the needle is inserted within the housing of the incinerator, regardless of the size of needle, contact is ensured with the contacts so that a complete disintegration of the needle takes place substantially instantaneously thereby converting the metal to a harmless residue with all toxic substances and pathogens completely destroyed.

It is yet a further object of the present invention to provide an incinerator device which may be safely used in homes, hospitals, doctors and dentist offices, health care and drug treatment facilities, wherein the incinerating device can not be accidentally activated and wherein the incinerating device is automatically deactivated in the event of tampering.

It is also an object of the invention to provide a needle incinerating apparatus which is electrically operated and which includes an indexing device for regulating the size of opening through which various sizes of syringes may be inserted so that needles extending therefrom may be engaged by a pair of electrical contacts which are operable to supply sufficient voltage to disintegrate the needles upon contact.

BRIEF DESCRIPTION OF THE DRAWINGS

FIGS. 8–11 are illustrational views showing the insertion of a hypodermic needle into engagement with the contact elements for disintegrating the needle in accordance with the teachings of the present invention without the indexing member of the invention being shown.

DESCRIPTION OF THE PREFERRED EMBODIMENT

Figure 1:
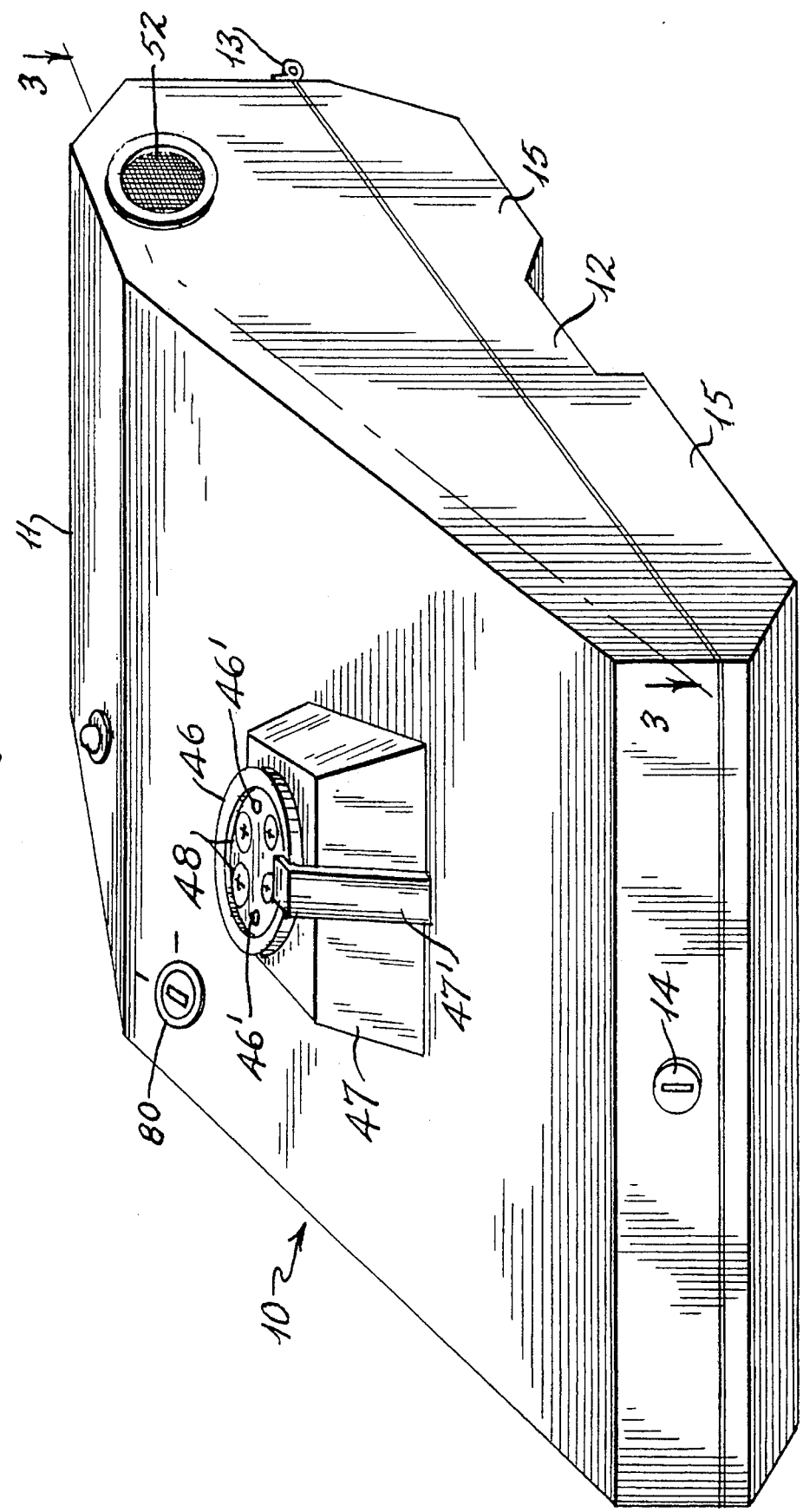
FIG. 1 is a front perspective view of the incinerator of the present invention.
Figure 2:
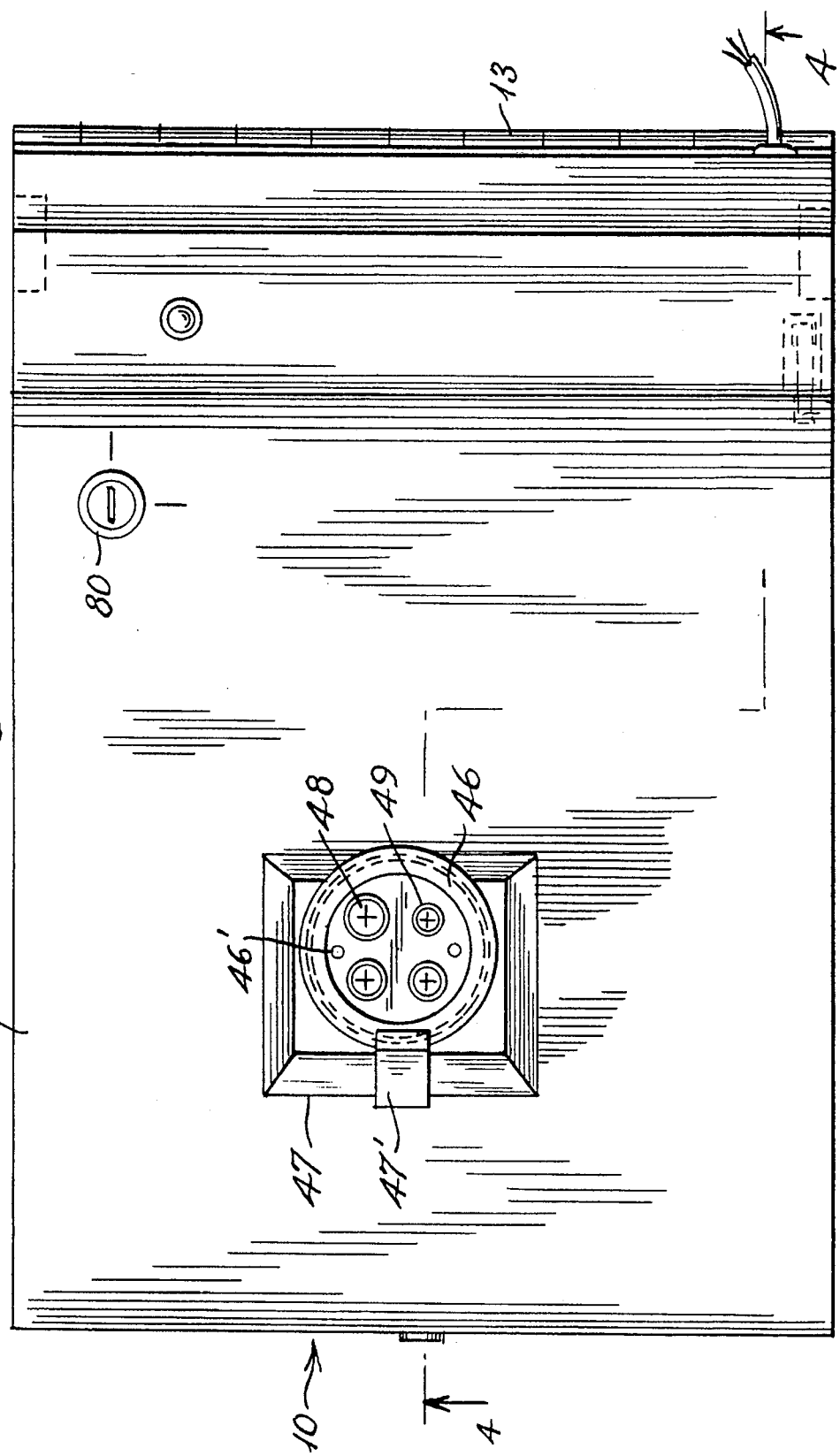
FIG. 2 is a top plan view of the incinerator of the present invention.

With continued reference to the drawing figures, the needle incinerator 10 of the present invention includes a housing defined by an upper cover 11 which is pivotably connected to a base 12 by a hinge 13. The cover is preferably made from a high density PVC plastic material which is flame retardant. The incinerator is relatively compact being less than approximately 26 cm in length and less than 23 cm in width. A key operated lock 14 is mounted through the front portion of the cover so as to normally retain the cover in a locked relationship with respect to the base so that accidental entry into the incinerator is prohibited. The base includes a plurality of integrally formed support legs 15 which elevate the base slightly above the support surface. A plurality of air inlet slots 16 are provided through the front portion of the base for allowing air to be drawn into the incinerator during its use. It should be note, in some instances, the air vents may be provided through a portion of the front of the cover as opposed to being disposed in the front portion of the base. This would be particularly true when the unit is adapted to be mounted directly to a wall surface as opposed to being supported on a table or other horizontal surface. In some embodiments, an appropriate seal is provided along the perimeter between the base and the cover.

The interior of the incinerator is divided by two interior partitions 18 and 19 also formed of high density PVC. Each partition includes a plurality of openings 18' and 19' to allow the passage of air and gas therethrough. Mounted to the front portion of partition 18 is a filter assembly 20 which includes a filter retainer frame 21 constructed of the same material as the partition 18 and which slidingly receives a filter element 22 which is in a size to cover the openings 18'. The filter element may be a carbon fiber filter or HEPA filter for purifying air entering the incinerator through the slots or openings 16. The spaced openings 19' provided through partition 19 are covered by a pair of filter assemblies 23 which include filter retaining frames 24 in which slidable filter elements 25 are selectively received. Each filter assembly 23 is of a size to ensure that the openings 19' are completely covered.

Figure 3:
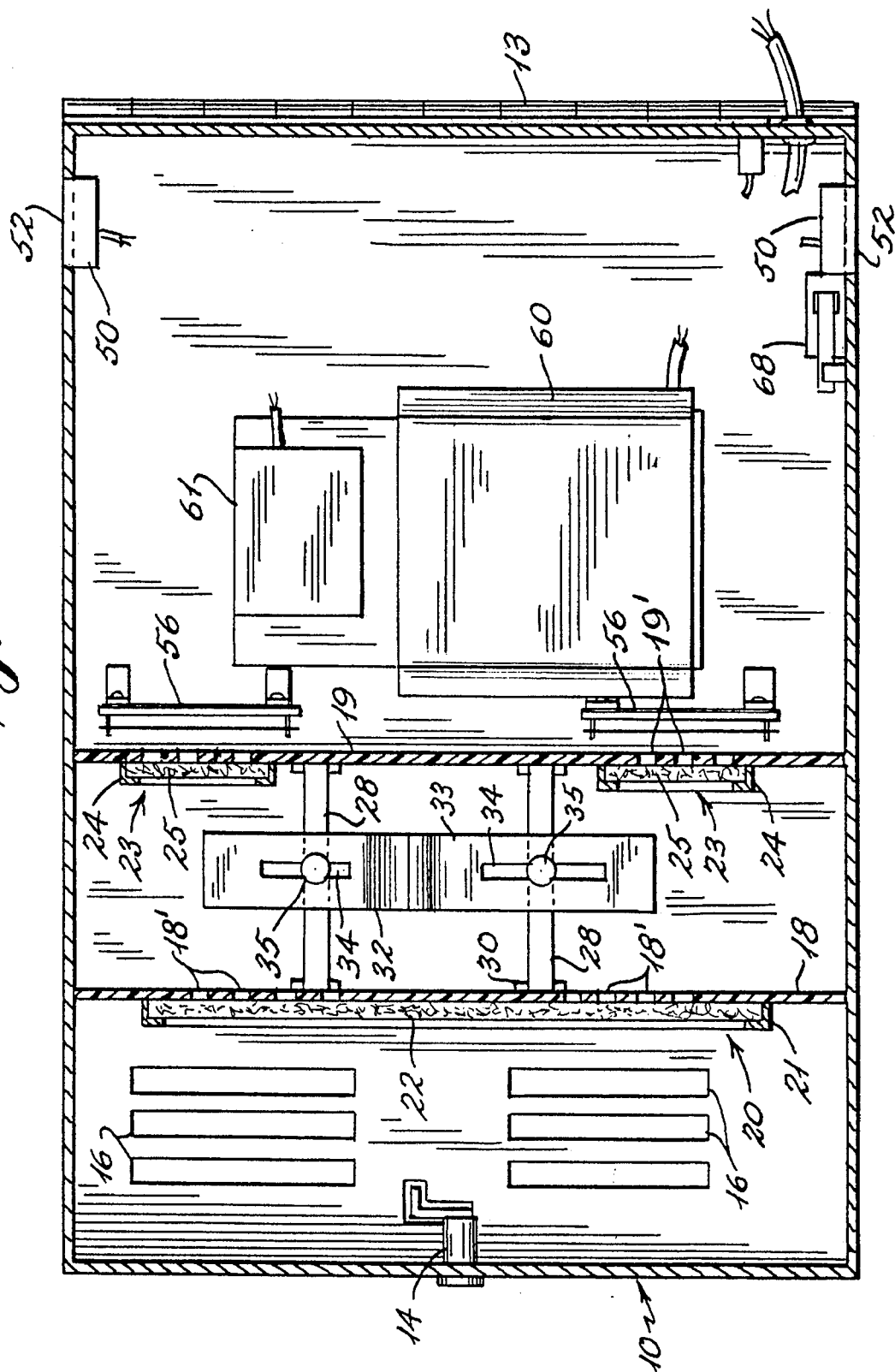
FIG. 3 is a sectional view taken along line 3—3 of FIG. 1.

With specific reference to FIG. 3 the area between the interior partitions 18 and 19 defines a combustion or incinerator chamber 26. A pair of generally horizontal supports 28 extend between the partitions 18 and 19 and are supported at there opposite ends in vertically arranged racks 30 having a plurality of spaced grooves therein in which the ends of the supports 28 may be frictionally retained. In this manner, each of the supports 28 may be independently raised or lowered within the chamber 26.

Supported on the members 28 are a pair of opposing incinerator contacts or electrodes 32 and 33 which are preferably constructed of a copper material. Each contact has a longitudinal slot 34 therein by way of which the contacts are slidably supported relative to mounting pins 35 which are threaded through the support members 28. As the pins 35 have enlarged heads, it is not possible for the electrical contacts to be withdrawn from an adjusted relationship with respect to the supports 28. As the pins 35 are threadingly mounted to support members 28, the contacts may be fixedly secured in an adjusted position.

Figure 5:
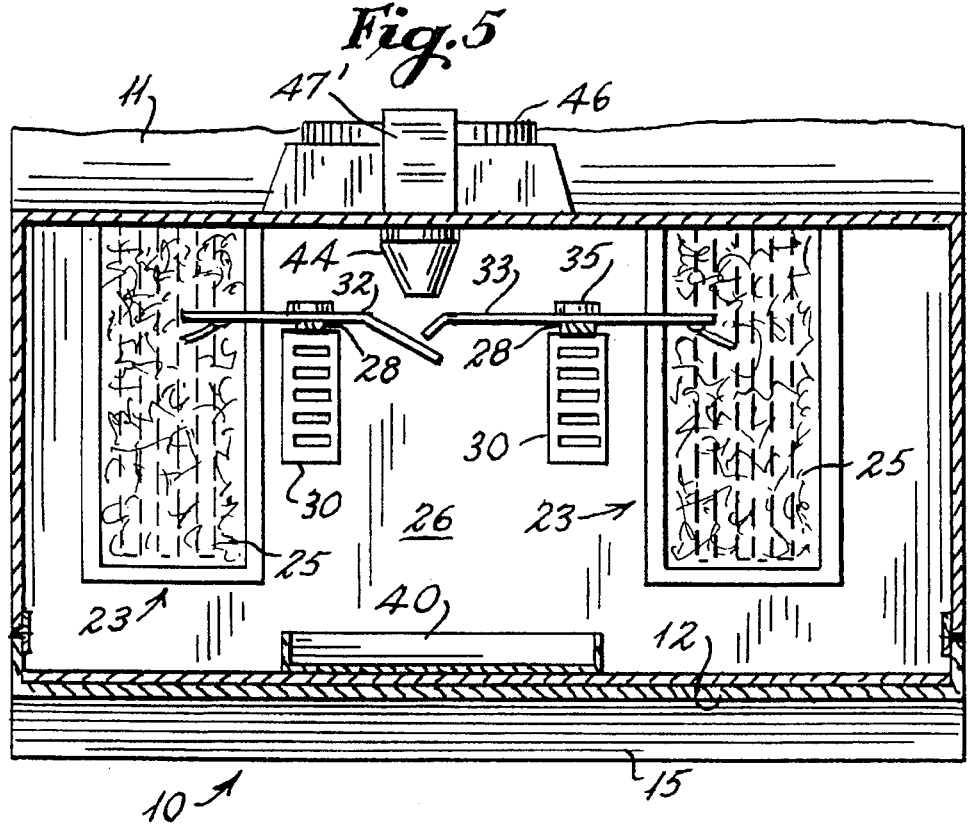
FIG. 5 is a cross-sectional view taken along line 5—5 of FIG. 4.
Figure 6:
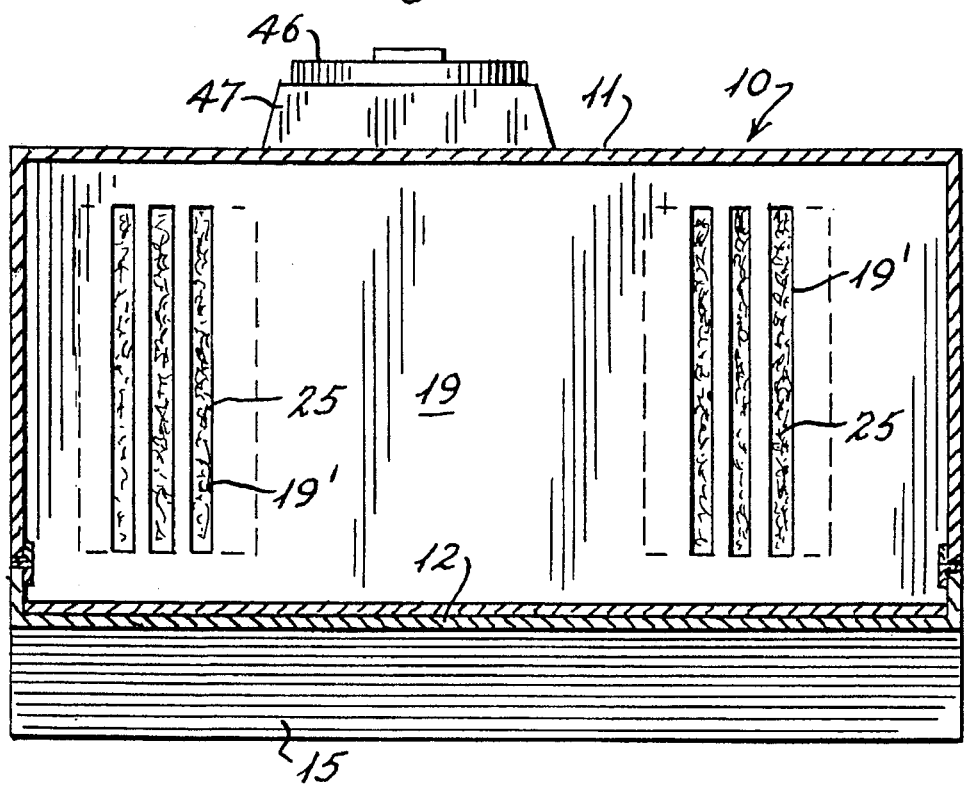
FIG. 6 is a cross-sectional view taken along line 6—6 of FIG. 4.

As noted in FIG. 5, electrical contact 32 has an end portion 32' which depends at an oblique angle with respect to the slotted body portion of the contact so as to underlie an obliquely depending end portion 33' integrally formed with contact element 33. In this manner, the contact elements overlap each other in a vertical plane. Both of the depending end portions 32' and 33' are preferably coated with a silver plating. Each contact is electrically connected to a source of electrical power as will be described in greater detail hereinafter. From the foregoing, it is possible to adjust the relationship between the contacting end portions 32' and 33' of the electrical contacts 32 and 33 both horizontally with respect to one another as well as vertically. In this manner, it is possible to adjust the spacing between the contact end portions depending upon the average size of needle which is to be destroyed utilizing the incinerator of the present invention. It should further be noted that the electrical contacts are relatively yieldable or resilient so as to allow a hypodermic needle to initially make contact with the contact end portion 33' before engaging against the contact end portion 32'. Once contact is established between both contacts or electrodes an electric arc is created between the contacts through the needle thereby instantaneously oxidizing the needle to form a generally harmless powder residue. Mounted within the incinerator chamber 26 is a stainless steel receptacle or tray 40 which receives the residue material resulting from the incineration process.

Figure 4:
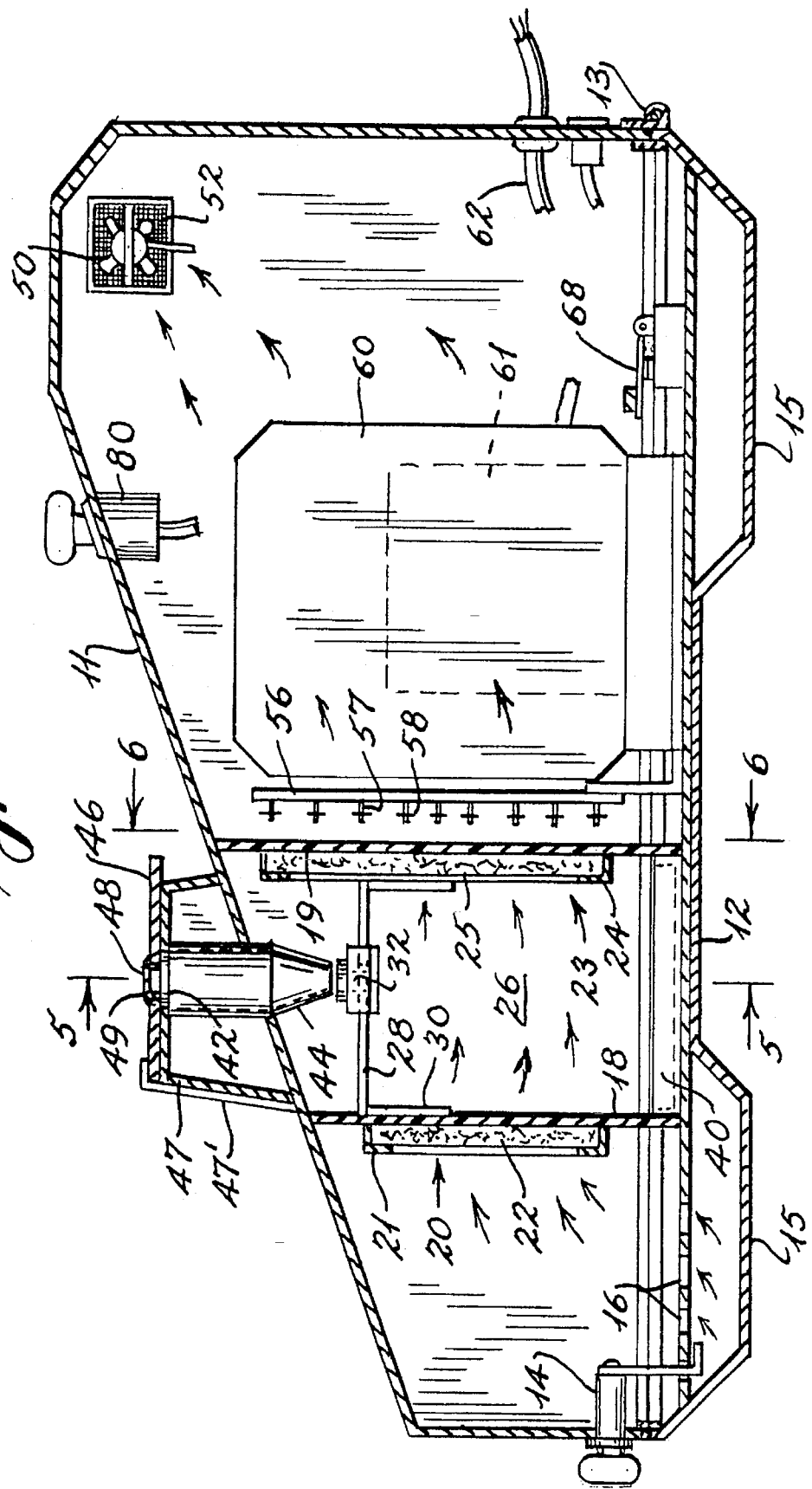
FIG. 4 is a cross-sectional view taken along line 4—4 of FIG. 2.

In order to insert a needle into electrical contact with the electrodes 32 and 33, a syringe opening 42 is provided through a raised portion 47 of the cover 11 in vertical alignment above the tip portions 32' and 33' of the electrical contacts. To guide the tip of a hypodermic syringe relative to the electrodes, an insertion guide member 44 is mounted in surrounding relationship to the opening 42 and extends inwardly toward the electrodes 32 and 33. As shown in FIG. 4, the guide element is generally funnel shaped in configuration and serves as a stop to limit the distance that the tip of the hypodermic syringe "H" may be inserted into the incinerator chamber 26, as shown in dotted line in FIG. 10. Due to the tapering configuration of the sidewalls of the guide element, a relatively tight seal is also established between the tapered tip of a conventional hypodermic syringe and the guide element. This contact facilitates the sealing of the opening 42 with respect to the chamber 26 whenever a needle is being incinerated. The guide member also functions as a spark shield to prevent any electrical arc from extending to the opening 42.

In the preferred embodiment of the present invention, the guide element 44 cooperates with an outer indexing member 46. The indexing member is rotatably mounted on the raised portion 47 of the cover in offset relationship with respect to the opening 42. A plurality of spaced openings 48 of different diameters are formed in the indexing member. The openings 48 are designed to be indexed into aligned relationship with the opening 42 and thus with the guide member 44 by selectively rotating the indexing member 46 to an appropriate position. Detents 46' are provided as the indexing member which frictional seat is depressions formed in the raised portion 47 of the cover. A hold down area 47' is provided to place pressure downwardly in the indexing member, as shown in FIGS. 1 and 4. In this respect, the indexing mechanism allows for the controlled or stabilized insertion of hypodermic syringes having different diameter barrels. In addition, in some embodiments, grommets are other sealing devices 49 may be associated with each of the openings 48 so that when a hypodermic syringe is inserted therethrough, the syringe will be sealed in relationship with respect to the openings 48 thereby preventing the escape of any combustion gases upwardly therethrough as a needle is being incinerated.

With specific reference to FIG. 4, once a needle has been incinerated within the chamber 26, the exhaust gases are evacuated by a pair of pancake fans 50 which are mounted along the rear sidewalls of the cover 11 and on opposite sides thereof. A plurality of exhaust openings 52 are made through the opposite sides of the cover adjacent the upper and rear portion thereof. The fans are of a size to ensure that a reduced pressure is positively maintained within the combustion chamber at all times during the combustion process and until such time as all combustion gases have been exhausted from the incinerator. In some embodiments, it is possible to electrically activate the fans 50 in response to a hypodermic needle being inserted through the indexing member and into contact with the electrodes 32 and 33. Such a mechanism would thereafter maintain the fans in an ON condition for a specific period of time to ensure that all combustion gases within the incinerator are properly treated before being exhausted afterwhich the fans would be automatically deactivated.

With the present invention, the combustion gases are not only filtered by the filters 25 but the air is thereafter passed into contact with a pair of ionizers 56 which have a plurality of contact elements 57 and 58 extending therefrom which are oppositely charged. The ionizers are designed to be electrically activated at approximately 2500 volts and serve to ensure that any trace elements in the exhaust gases are completely eliminated prior to the exhaust gas being evacuated through the exhaust openings 52. In this manner, trace elements of such potentially hazardous metals including mercury and cadmium as well as various silicates are substantially totally eliminated by the ionizers. Testing has determined that the exhaust from the exhaust openings 52 meets standards established for clear air environments, such as in hospital operating rooms.

Figure 7:
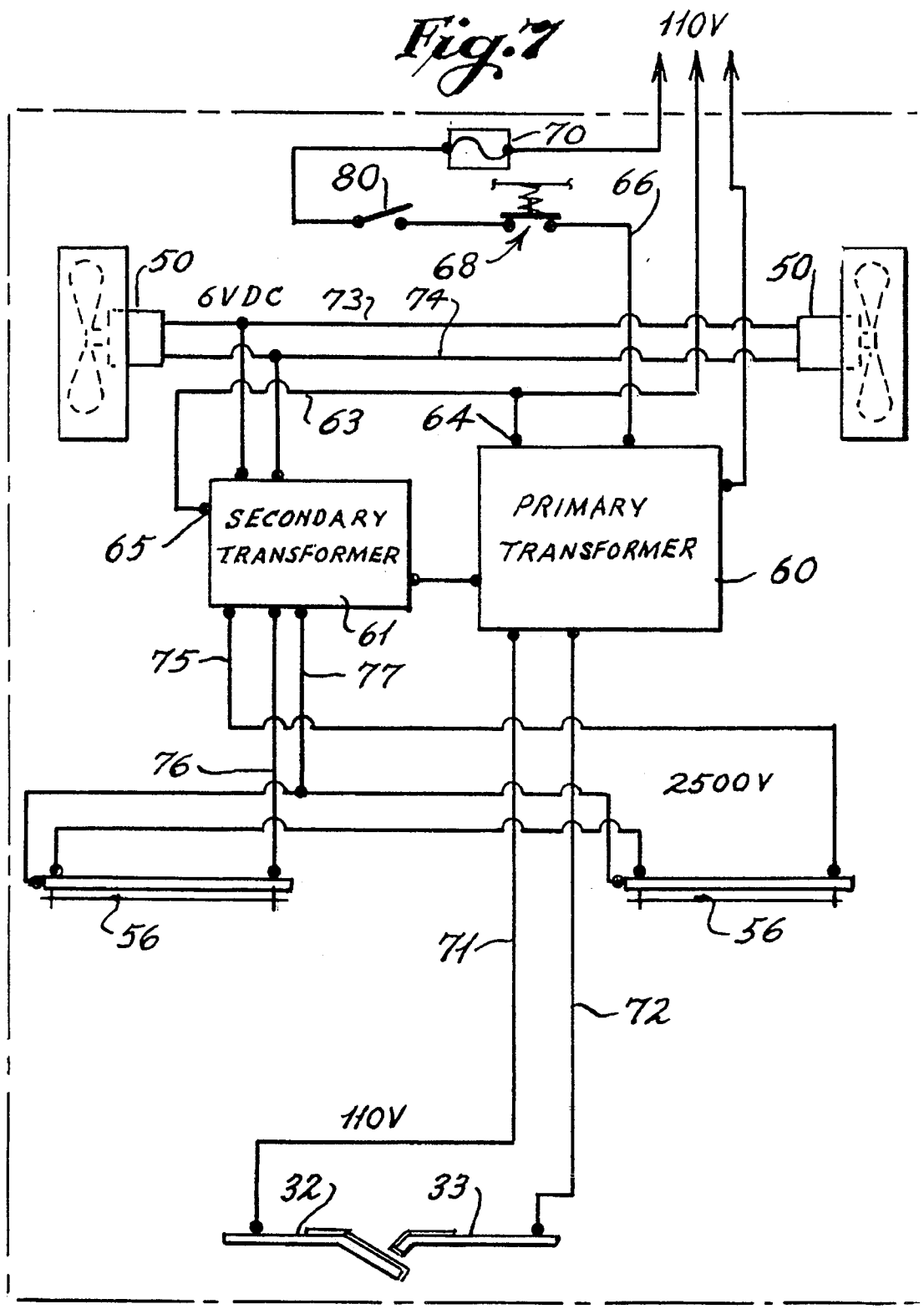
FIG. 7 is an electrical schematic diagram of the power control circuit of the present invention.

As shown in FIG. 7, to supply electrical power to the electrical contacts 32 and 33, the fans 50 and the ionizers 56, the incinerator of the present invention includes a primary transformer 60 and a secondary transformer 61. Power is obtained from a conventional 110 volt AC outlet through a conventional multi-wire conductor 62 which is connected through a power input line 63 to the secondaries 64 and 65 of the primary and secondary transformers. Each of the transformers are further connected to ground through a ground line 66 which is interrupted by a microswitch 68 which is operable to open the electrical circuit from ground thereby terminating power through the transformers anytime an attempt is made to raise the cover 11 relative to the base 12. The microswitch is installed generally adjacent the rear portion of the unit so as to be responsive to the slightest movement of the cover relative to the base. The ground wire 66 is also connected through an appropriate fuse arrangement 70 to ground.

Power supply to the electrodes 32 and 33 is from the primary transformer 60 through input lines 71 and 72. Approximately 800 volts is established between the contacts by the transformer. Power to the fans and to the ionizers is provided through the secondary transformer with 7 volts of DC stepdown power being provided to each of the fans 50 through electrical lines 73 and 74. The secondary transformer is also utilized to provide a high voltage (2500 volts) to each of the ionizers through lines 75 and 76 and ground line 77. Both the fans and the ionizers are also connected back through the secondary transformer to ground.

One of the advantages of the present invention is that the electronic circuit can only be activated by an individual having the ability to access the incinerator control circuit by way of a key or control card. This prohibits the incinerator from being utilized by unauthorized individuals or accidentally activated by persons tampering with the equipment.

Mounted to the cover 11 is a key switch 80 which is directly connected in line with ground wire 66. Unless the key switch is turned to an ON position the circuit is OFF at all times. Only with the proper access key can the operator turn the key to the ON position to activate or to allow power to be supplied to the transformers for energizing the electrodes, ionizers and fans. As opposed to using a key ON/OFF switch, it is envisioned that an appropriate coded card or similar device could also be utilized to activate the circuity of the present invention.

From the foregoing, it may be seen that the incinerator of the present invention may be safely used to dispose of dangerous, contaminated and potentially toxic needle elements utilized in a plurality of environments. By simply activating the incinerator by utilizing an activation key, the operator need only rotate the indexing mechanism to the proper size for the hypodermic syringe being used and thereafter insert the syringe, needle end first, into the indexing mechanism until such point as the needle engages the tip portions of the contacts 32 and 33. The electrical arc between the contacts completely oxides the metallic material substantially instantaneously, within less than one to two seconds, at an operating temperature of 1000° C. or greater being created by the electrical arc. The guide element 44 will prevent further penetration of the hypodermic syringe into the combustion chamber 26. The fans will draw the combustion gases through the filters 25 and across and between the surface of the ionizing elements of the ionizers 60 after which the purified exhaust gas is vented to atmosphere. In the event adjustment to the electrodes is necessary, such adjustment may be easily made upon accessing the interior of the incinerator. As soon as the cover to the incinerator is raised relative to the base, the entire unit is electrically deactivated so that accidental injure will not occur. Periodically, the tray within the combustion chamber may be removed and the debris therein safely disposed.

With specific reference to FIGS. 8–11, an alternate embodiment of the present invention is disclosed in greater detail. These drawings figures also clearly illustrate the manner in which a needle "N" is disintegrated by making electrical contact between the tips of the electrical contacts 32 and 33. In this embodiment, the indexing member 46 and raised portion 47 of the cover have been eliminated. The hypodermic opening 42' is provided directly in the planar surface of the cover and the guide member 44' extends directly inwardly from the opening 42'. As with the previous embodiment, a gasket, or other sealing device 49' may be provided at the opening 42'. The guide member will serve to limit the degree to which the hypodermic syringe may be inserted relative to the contacts and also provides an arc safety shield. As shown in FIGS. 10 and 11, once the needle makes contact between the electrical contacts 32 and 33, the needle is instantly disintegrated into a safe and handable debris.

We claim:

1. An incinerator apparatus for disintegrating a needle connected to a hypodermic syringe comprising, a housing having ambient air inlet and at least one exhaust outlet, a combustion chamber within said housing, a pair of spaced electrical contacts mounted within said combustion chamber, an opening in said housing and aligned with said electrodes through which a needle connected to a hypodermic syringe may be inserted so as to selectively contact the needle with said contacts, fan means mounted within said housing for drawing air through said inlet and exhausting air through said at least one outlet, at least one exhaust filter means mounted within said housing between said combustion chamber and said at least one exhaust outlet, at least one ionizer means mounted within said housing between said combustion chamber and said at least one exhaust outlet, whereby exhaust gases are filtered through said at least one exhaust filter means and ionized by said at least one ionizer means before being exhausted by said fan means through said at least one exhaust outlet, and energizing means mounted within said housing for supplying electrical energy to said contacts, said at least one ionizer means, and said at least one fan means, and switch means mounted to said housing for activating said energizing means.

2. The incinerator apparatus of claim 1 including an insertion guide means mounted within said combustion chamber and in alignment with said opening in said housing, said insertion guide means including tapering wall portions for limiting the insertion of a hypodermic syringe within said combustion chamber.

3. The incinerator apparatus of claim 2 including an indexing means mounted exteriorly of and to said housing, said indexing means including a plurality of secondary openings therethrough of varying dimensions, said indexing means being adjustable to align a selected secondary opening with said opening in said housing whereby said secondary openings positively guide hypodermic syringes of differing diameters into said combustion chamber.

4. The incinerator apparatus of claim 3 in which each of said secondary openings is tapered inwardly toward said opening in said housing.

5. The incinerator apparatus of claim 3 including seal means mounted within each of said secondary openings for sealing said openings when a hypodermic syringe is extended therethrough.

6. The incinerator apparatus of claim 2 including means for horizontally adjusting the spacing between said electrodes within said combustion chamber.

7. The incinerator apparatus of claim 6 in which each of said contacts includes a depending end portion, said depending end portions being in spaced vertical relationship with respect to one another, an open slot in each of said contacts, means for supporting said contacts within said combustion chamber, and means extending through said open slots for selectively securing said electrodes in an adjusted position.

8. The incinerator apparatus of claim 7 including means for vertically adjusting said contacts within said combustion chamber.

9. The incinerator apparatus of claim 1 including means for horizontally and vertically adjusting said contacts within said combustion chamber.

10. The incinerator apparatus of claim 1 in which said switch means includes a lockout, an activation means for activating said lockout to provide electrical power to said energizing means.

11. The incinerator apparatus of claim 10 in which said housing includes a cover portion and a base portion, means for mounting said cover portion to said base portion, and lock means for securing said cover portion to said base portion.

12. The incinerator apparatus of claim 11 including a second switch means connected to said energizing means, said second switch means being operable to turn OFF said energizing means in the event said cover portion is open relative to said base portion.

13. The incinerator apparatus of claim 12 including prefilter means mounted within said housing, said pre-filter means being mounted between said inlet opening and said combustion chamber for filtering air being drawn into said combustion chamber.

14. The incinerator apparatus of claim 13 including first and second exhaust filter elements mounted within said housing between said combustion chamber and said at least one exhaust outlet, and first and second ionizer means mounted in fluid communication with said first and second exhaust filter means whereby all gases from said combustion chamber must pass through said first and second exhaust filter means and in contact with said first and second ionizer means before being exhausted through said at least one exhaust outlet.

15. The incinerator apparatus of claim 14 including first and second exhaust outlets in said housing, and first and second fan means for directing exhaust air through said exhaust outlets.

16. The incinerator apparatus of claim 15 in which said energizing means includes a first transformer means for supplying electrical power to said contacts and a second transformer means for supplying power to said first and second ionizer means and said first and second fan means.

17. An incinerator apparatus for disintegrating a metallic needle mounted to a hypodermic syringe including a housing, said housing including a cover portion and a base portion, means for selectively locking said cover portion relative to said base portion, said housing including an ambient air inlet and at least one exhaust outlet, a combustion chamber mounted within said housing, means for adjusting the spacing between a pair of electrical contacts mounted within said combustion chamber, an opening in said housing in alignment with said electrodes, a hypodermic syringe insertion guide means mounted within said housing in alignment with said opening and said contacts for limiting the degree of insertion of a hypodermic syringe with respect to said contacts, an exhaust filter means mounted within said housing through which exhaust gases from the combustion chamber must pass, at least one ionizer means mounted between said combustion chamber and said exhaust outlet for ionizing exhaust gases before they are exhausted through said at least one exhaust outlet, at least one fan means mounted within said housing for drawing air from said air inlet through said at least one exhaust outlet, an electrical energy supply means mounted within said housing and including a first transformer means for energizing said contacts and second transformer means for activating said at least one ionizer means, switch means for activating said energy supply means and including a lockout means and means for activating said lockout means, and a power cut-off switch mounted between said cover portion and said base portion for terminating power to said first and second transformers in the event said cover portion is open relative to said base portion.

18. The incinerator apparatus of claim 17 including an indexing means mounted exteriorly of and to said housing, said indexing means including a plurality of secondary openings therethrough of differing dimensions, said indexing means being movable to align a selected one of said secondary openings with said opening in said housing.

19. The incinerator apparatus of claim 18 including a prefilter means mounted within said housing for filtering air entering through said air inlet means and passing into said incinerator chamber, a pair of exhaust filter means mounted between said incinerator chamber and said at least one exhaust outlet, a pair of ionizer means mounted adjacent said exhaust filter means for ionizing the air passing through said exhaust filter means.

20. The incinerator apparatus of claim 17 including means for horizontally and vertically adjusting said contacts within said combustion chamber.

* * * * *